(12) United States Patent
Wood

(10) Patent No.: US 7,753,457 B2
(45) Date of Patent: Jul. 13, 2010

(54) APPARATUS FOR REMOVABLY RETAINING A SLIDE WITHIN A CASSETTE

(75) Inventor: Nathan P. Wood, Winchendon, MA (US)

(73) Assignee: Cytyc Corporation, Marlborough, MA (US)

( * ) Notice: Subject to any disclaimer, the term of this patent is extended or adjusted under 35 U.S.C. 154(b) by 206 days.

(21) Appl. No.: 10/459,881

(22) Filed: Jun. 12, 2003

(65) Prior Publication Data
US 2004/0251796 A1    Dec. 16, 2004

(51) Int. Cl.
A47B 81/06    (2006.01)
(52) U.S. Cl. .................. 312/9.51; 312/9.57; 312/319.1
(58) Field of Classification Search .................. 312/9.1, 312/9.9, 9.47, 9.48, 9.51, 9.57, 9.64, 319.1, 312/334.44; 206/309, 387
See application file for complete search history.

(56) References Cited

U.S. PATENT DOCUMENTS

| | | | | |
|---|---|---|---|---|
| 655,020 | A | * | 7/1900 | Schroeder ................. 312/319.1 |
| 4,367,915 | A | * | 1/1983 | Georges ..................... 359/385 |
| 4,678,245 | A | * | 7/1987 | Fouassier ................... 312/9.22 |
| 4,771,887 | A | * | 9/1988 | Nehl ...................... 206/387.15 |
| 4,819,802 | A | * | 4/1989 | Gutierrez ............... 206/387.15 |
| 4,844,564 | A | * | 7/1989 | Price et al. .................. 312/9.46 |
| 5,183,177 | A | * | 2/1993 | Yu .............................. 220/523 |
| 5,320,244 | A | * | 6/1994 | Yu .............................. 220/507 |
| 5,393,135 | A | * | 2/1995 | Tisbo et al. ................ 312/9.48 |
| 5,505,299 | A | * | 4/1996 | Ditzig et al. ............. 206/308.1 |
| 5,690,892 | A | * | 11/1997 | Babler et al. ................... 422/63 |
| 5,871,696 | A | * | 2/1999 | Roberts et al. ................ 422/65 |
| 5,931,295 | A | * | 8/1999 | Kaupp ..................... 206/308.1 |
| 6,361,745 | B1 | * | 3/2002 | Regan et al. ................ 422/104 |
| 6,395,554 | B1 | * | 5/2002 | Regan et al. .................. 436/46 |
| 6,534,017 | B1 | * | 3/2003 | Bottwein et al. ............ 422/104 |
| 6,847,481 | B1 | * | 1/2005 | Ludl et al. .................. 359/391 |

(Continued)

FOREIGN PATENT DOCUMENTS

DE    297 12 535    9/1997

(Continued)

OTHER PUBLICATIONS

PCT International Search Report for PCT/US2004/016945, Applicant Cytyc Corporation, Forms PCT/ISA/210 and 220, dated Nov. 11, 2004 (8 pages).

(Continued)

*Primary Examiner*—Hanh V Tran
(74) *Attorney, Agent, or Firm*—Vista IP Law Group LLP

(57) ABSTRACT

Apparatus and slide cassette for removably retaining or securing a slide. The cassette includes trays for holding a slide. Each tray has a retaining lip at an end thereof. A first edge of a slide contacts a support member within the cassette when the slide that is placed in a slot. The support member can be an elastomeric member, a spring, a foam member, or an insert with slide retention surfaces. The support member pushes or urges the slide in the opposite direction so that an opposite edge of the slide contacts the retaining lips of the trays. As a result, the slide is removably retained or secured on the trays and between the retaining lips and the support member(s).

13 Claims, 15 Drawing Sheets

U.S. PATENT DOCUMENTS 7,140,738 B2 * 11/2006 Guiney et al. ............... 353/103

FOREIGN PATENT DOCUMENTS

| | | |
|---|---|---|
| GB | 1 593 064 | 7/1981 |
| WO | WO 02/075425 | 9/2002 |
| WO | WO 02/081089 | 10/2002 |
| WO | WO 03/038504 | 5/2003 |

OTHER PUBLICATIONS

PCT Written Opinion of the International Search Authority for PCT/US2004/016945, Applicant: Cytyc Corporation, Form PCT/ISA/237, dated Nov. 11, 2004 (5 pages).

* cited by examiner

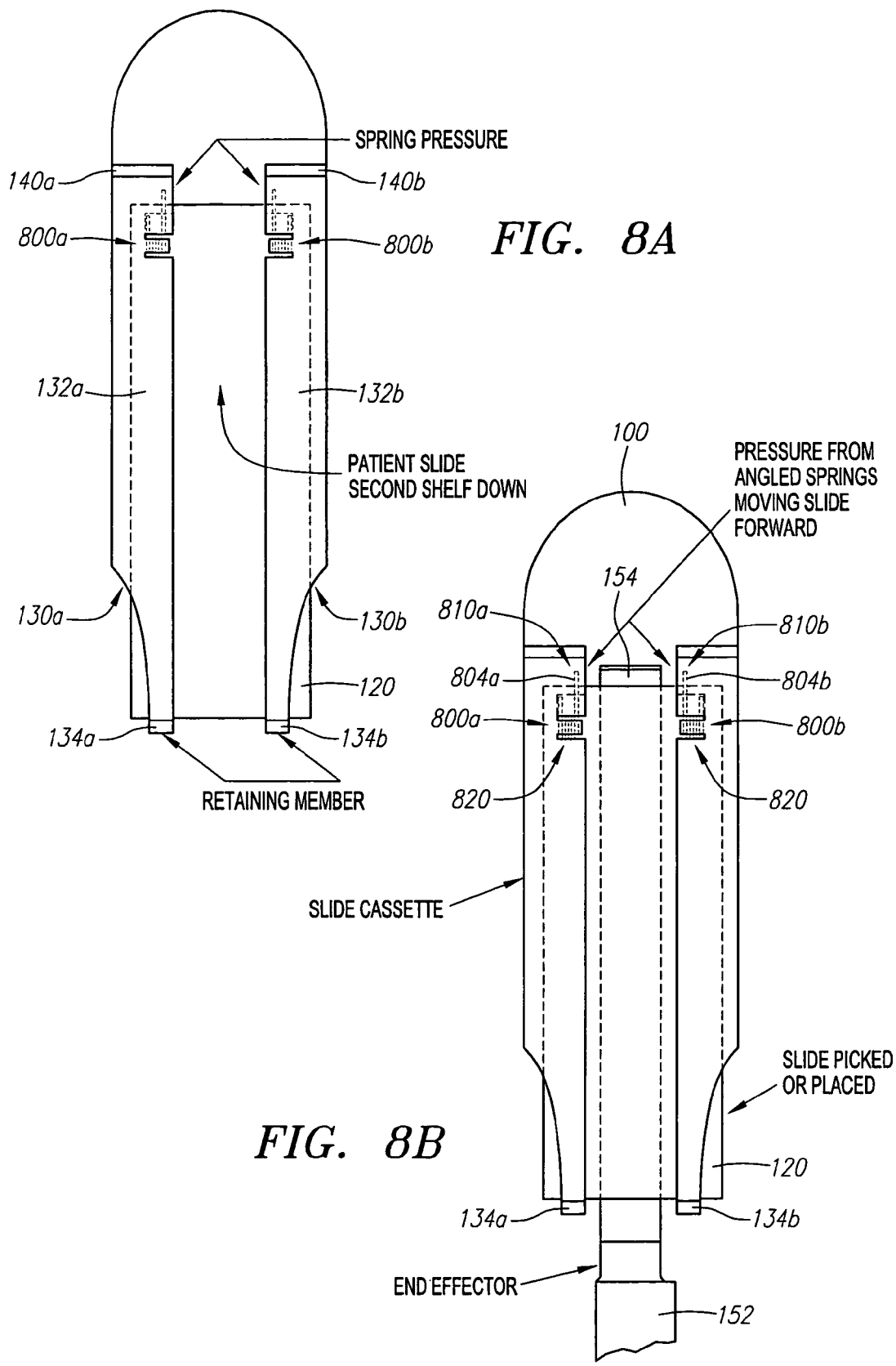

APPARATUS FOR REMOVABLY RETAINING A SLIDE WITHIN A CASSETTE

FIELD OF THE INVENTION

The present invention relates to test slide holders, and more particularly, to an apparatus for removably retaining or securing a slide within a cassette utilizing a support member inside the cassette.

DESCRIPTION OF RELATED ART

Various devices have been used to store glass slides, such as microscope and patient test slides. For example, one conventional storage apparatus is a tray or box that includes one or more slotted rows. Slides are manually inserted in an upright position between the slotted rows so that the ends of the slides are placed within slots. A slide can be manually removed by lifting the slide from the slots.

Another conventional storage device is a slide cassette. A cassette typically includes a pair of trays or fingers that extend from the side of the cassette and below a slot. A slide is typically placed on two trays. The end of each tray usually includes a retaining member that prevents the slide from falling from the outer ends of the trays. A slide is placed on the trays and inserted into a slot of the cassette. Each slot receives a single slide. The dimensions of a slot are typically larger than the dimensions of a slide so that the slide can be easily inserted into and removed from the slot. Larger slot dimensions also prevent damage to the slide and scratches to the sample on top of the slide. An automated or semi-automated analysis system removes the slides and positions them beneath a microscope or other device so a user can analyze the sample for cancer and other medical conditions. More specifically, the system grasps the slide, lifts it above the retaining members of the trays, removes the slide from the trays and the slot, and positions the slide beneath the microscope. The slide can be re-inserted into the slot after the analysis is completed.

Current slide cassettes, however, can be improved. First, some cassettes store slides in an unsecure manner and permit the slide to move or float freely upon the underlying trays. The retaining members at the outer edges of the trays prevent a slide from falling from the outer edges of the trays, but the retaining members are limited in this regard and usually are not effective in retaining the slide. As a result, a slide can shift from its original, intended position to various other, incorrect or less desirable positions, particularly since a cassette slot is typically larger than the slide. Consequently, an analysis system may not properly sense the position of a slide due to positioning and placement errors. Instead, the sensor for detecting slides may sense an incorrect position of the slide, resulting in inaccurate, erroneous or irrelevant data. Slides can also be damaged if an analysis system attempts to remove neighboring slides near incorrectly positioned slides from the cassette. Additionally, the extent that cassettes can be manually maneuvered or positioned into cassette station locations is limited since unsecured slides can be re-positioned, dislodged, and damaged. Finally, more sensitive or accurate processing or analysis components may be necessary in order to map and analyze additional slide locations resulting from shifting slides.

A need, therefore, exists for an apparatus that retains or secures slides in a cassette. The apparatus should also allow the slides to be efficiently removed from a cassette for testing or analysis, and re-inserted into the cassette as needed. A need also exists for a method of removably retaining a slide within a cassette.

SUMMARY OF THE INVENTION

In one embodiment, the present invention provides an apparatus for removably retaining or securing a slide within a storage receptacle, such as a slide cassette. A tray extends from the cassette and below a slot. An end of the tray has a retaining member. A support member located within the cassette is arranged so that a first edge of a slide contacts the support member when the slide is placed in a slot. The support member urges an opposite edge of the slide to contact the retaining member. As a result, the slide is removably retained on the tray between the retaining member and the support member. The support member can be substantially flexible, such as a foam member, elastomeric, a spring, or a plastic or polymer insert.

In further accordance with the present invention, a cassette includes a pair of trays extend from the slide cassette below a slot. Each tray has a retaining member. An elastomeric support member, such as a rubber band, is installed inside the cassette. A first edge of the slide contacts the elastomeric support member when the slide is placed in the slot. In response, the elastomeric support member urges an opposite edge of the slide to contact the retaining members. As a result, the slide is removably retained on the trays and between the retaining members and the elastomeric support member.

The elastomeric support member can be weaved through a plurality of mounting members to define a plurality of support member sections. For example, the mounting members can include first, second and third mounting points arranged in a triangular configuration. The elastomeric support member is wrapped partially around the first mounting point, between the first and the second mounting points, around the third mounting point at a top of the triangular configuration, and between a section of the elastomeric support member and the second mounting point. As a result, support member sections are formed between mounting points at a base of the triangular configuration.

In an alternative embodiment, a first elastomeric rubber member is placed through a first slot defined by a first tray within the slide cassette. A second elastomeric member is placed through a second slot defined by a second tray so that the first edge of the slide contacts both elastomeric members.

Also in accordance with the present invention, a cassette includes support member that are substantially flexible, such as a foam member. For example, foam members are applied to slide stops within the slide cassette. With this configuration, the first edge of the slide contacts the foam members when the slide is placed in the slot. The foam members urge an opposite edge of the slide to contact the retaining members, thereby removably retaining the slide on the trays and between the retaining members and the foam members.

In yet further accordance with the present invention, a cassette includes spring support members. Flanges of the springs are inserted within apertures of the trays. The springs are arranged so that the left and right portions of the first edge of a slide contact the springs. As a result, the springs urge an opposite edge of the slide to contact the retaining members, thereby removably retaining the slide on the trays and between the retaining members and the springs.

Also in accordance with the present invention, a cassette includes a support member that is an insert, such as a plastic, polymer or molded insert. The insert is installed within the cassette and can extend for the entire height of the cassette or a portion thereof. The insert defines grooves, and the slide stops are inserted within the grooves to secure the insert in the cassette The insert includes extensions or retention surfaces that function as springs. A first edge of a slide contacts the extensions when the slide is placed in the slot. The extensions urge an opposite edge of the slide to contact the retaining members, thereby removably retaining the slide between the retaining members and the extensions.

In further accordance with the present invention, a cassette includes a spring located within the cassette and a lever attached to the spring. The lever vertically extends within the cassette. The spring applies a force to the lever so that the lever contacts a first edge of a slide. As a result, the slide is removably retained on the trays between the retaining members and the lever. The lever can be configured to contact a plurality of slides.

BRIEF DESCRIPTION OF THE DRAWINGS

Referring now to the drawings in which like reference numbers represent corresponding parts throughout:

FIGS. 8A-C are top and side views of a cassette having coiled spring support members and the manner in which an end effector accesses a slide so secured;

DETAILED DESCRIPTION OF PREFERRED EMBODIMENTS

In the following description, reference is made to the accompanying drawings which form a part hereof, and which show by way of illustration specific embodiments in which the invention may be practiced. It is to be understood that other embodiments may be utilized as structural changes may be made without departing from the scope of the present invention.

Figure 1A:
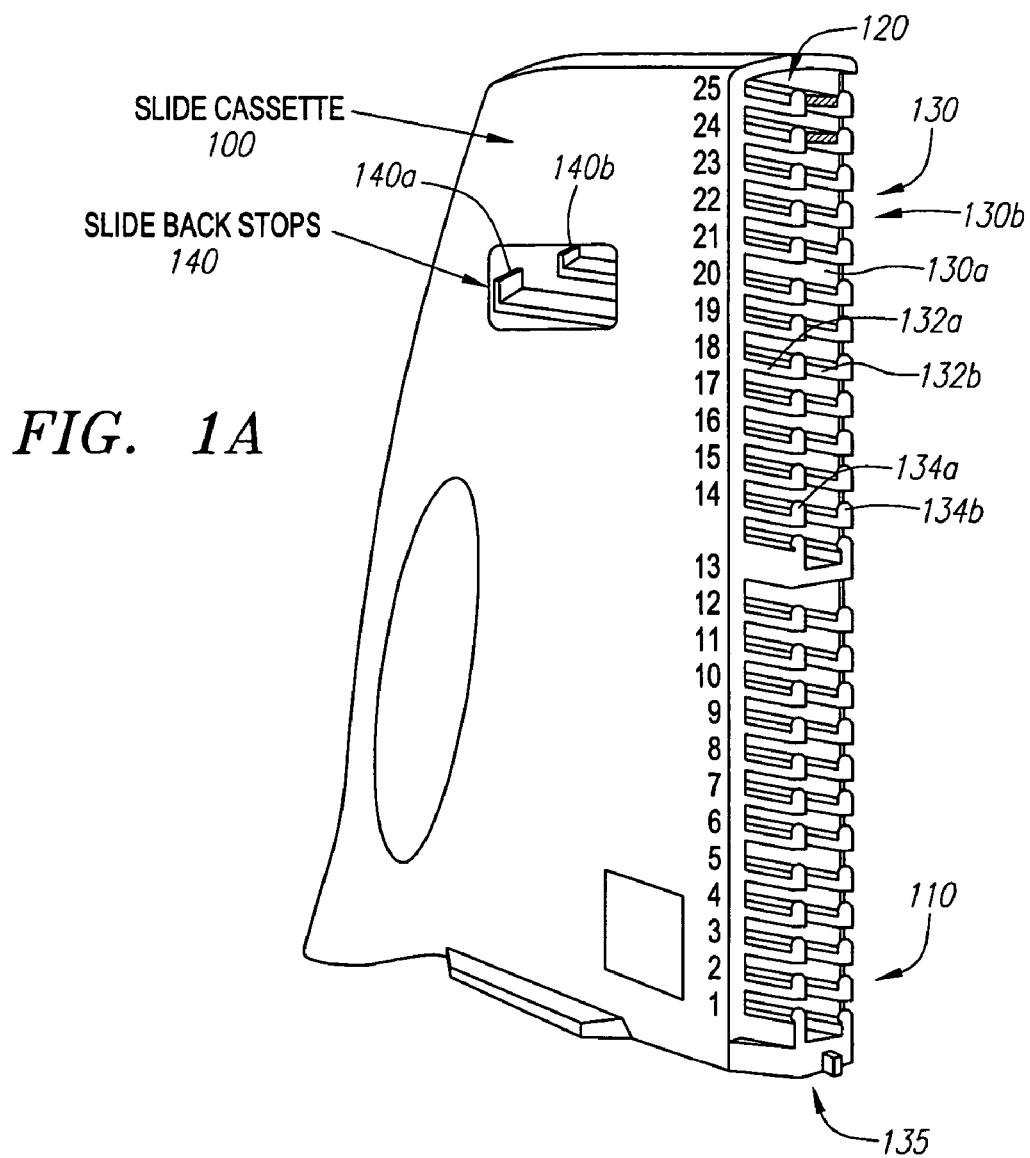
FIG. 1A is a perspective view of a cassette for storing slides.

Referring to FIG. 1A, an exemplary cassette 100 includes a plurality of horizontal slots 110 (e.g., slot numbers 1-25), slides 120 stored within the cassette, trays or fingers 130 that hold the slides and back stops or rear retaining walls 140 that limit how far a slide 120 can be placed in the cassette 100. Each slot 110 stores one slide 120.

Figure 1B:
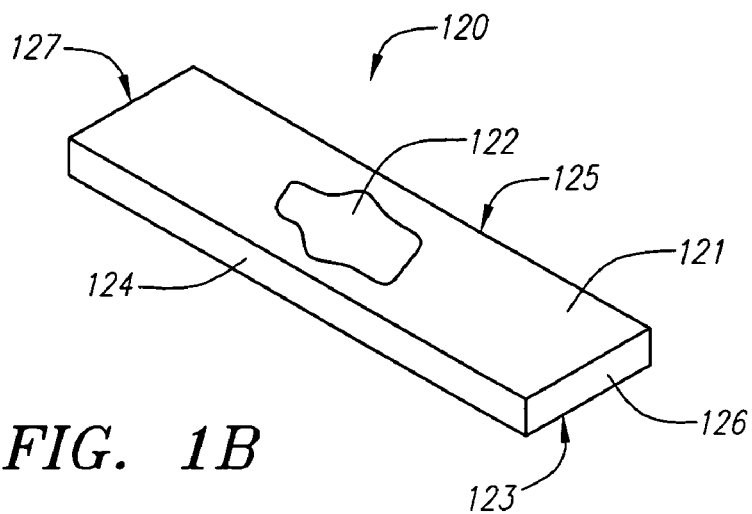
FIG. 1B is a perspective view of a slide having a test sample thereon.

As shown in FIG. 1B, a slide 120 has top surface 121 with a test sample or specimen 122, a bottom surface 123, a first side 124, a second or opposite side 125, a first edge 126 that is placed within a slot 110, and a second or opposite edge 127.

Figure 1C:
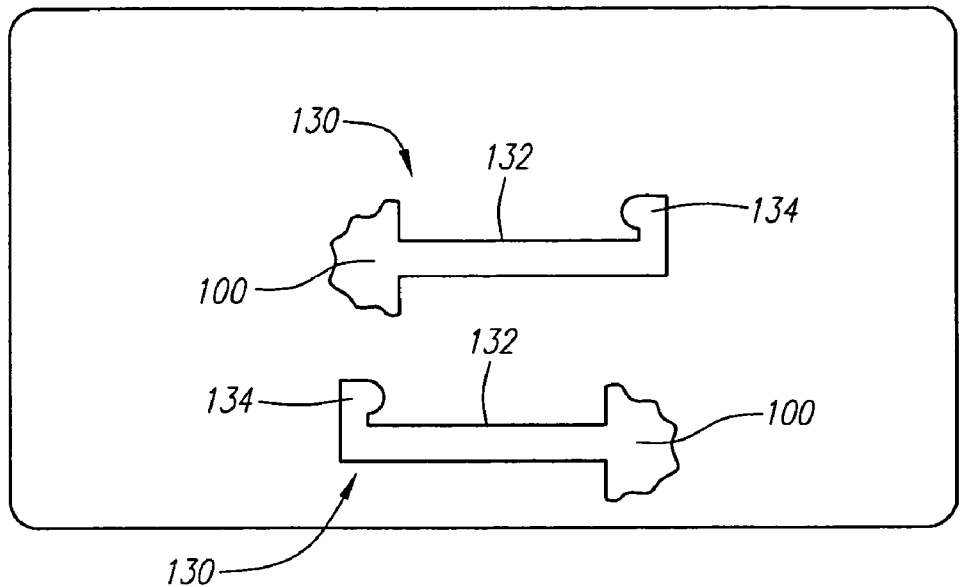
FIGS. 1C-D are respective partial side and top views of trays or fingers upon which a slide is placed.
Figure 1D:
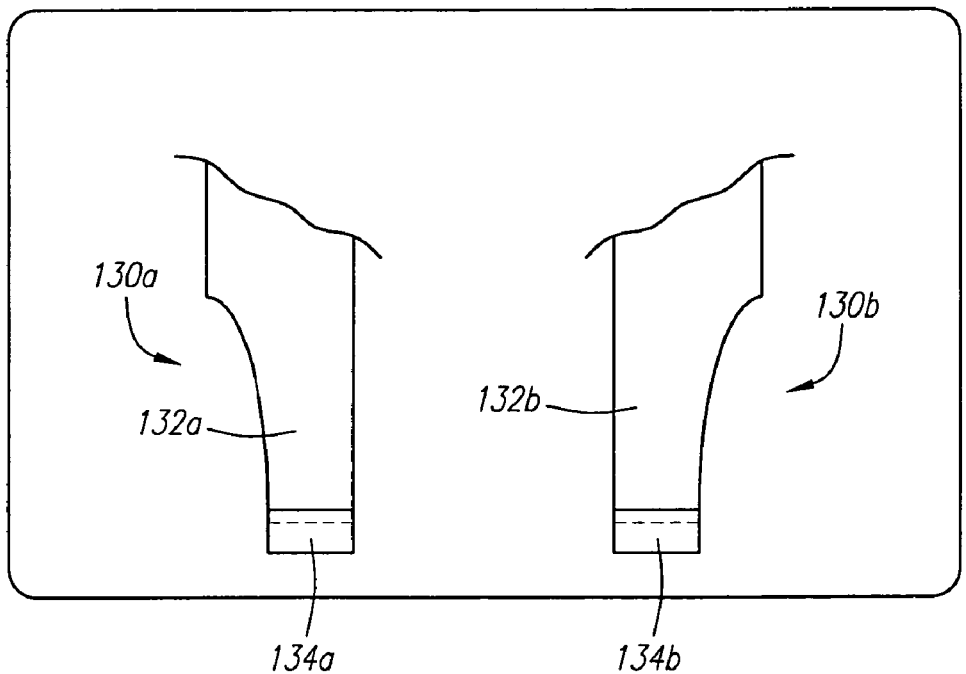

FIG. 1A illustrates one possible cassette 100 configuration in which a pair of trays of fingers 130a and 130b (generally 130) extend from the cassette 100 and below the slot 110 to hold a slide 120. The slide 120 is placed onto the top surfaces 132a and 132b (generally 132) of the trays 130 and into a slot 110. Movement of the slide within the cassette is limited by a pair of retaining walls 140a and 140b (generally 140) inside the cassette 100. The outer edges of the trays 130a and 130b include retaining members 134a and 134b (generally 134), such as a retaining lip. FIGS. 1C-D show side and top views of the trays 130 with retaining lips at the ends thereof. The retaining lips 134 prevent a slide 120 from falling from the trays 130 when, for example, the cassette 100 is tilted, repositioned, or adjusted.

One exemplary cassette 100 having the illustrated configuration is slide cassette part no. 70292-000, available from Cytyc Corporation, 85 Swanson Road, Boxbourough, Mass. 01719. This exemplary cassette 100 includes two trays 130 and two rear retaining walls 140 per slot 110. An analysis machine 150 (not shown in FIGS. 1A-B) can access a slide 120 stored in this exemplary cassette by inserting an access component, such as an end effector or effector arm 152 (not shown in FIGS. 1A-B) into the cassette slot 110. More specifically, the effector arm 152 is inserted through a middle gap 135 formed between the two trays 130a and 130b. The end effector 152 is elevated to capture or select a slide, and the slide 120 is laterally secured by a raised edge 154. The bottom surface 123 of the slide 120 is placed on a top or slide surface 156 of the end effector 152. The end effector 152 and the slide 120 are lifted over the retaining members 134 of the trays 130.

Persons of ordinary skill in the art will recognize that various tray 130 and retaining wall 140 arrangements can be utilized depending on the manner in which an analysis system accesses slides in the cassette 100. For example, as previously discussed, the cassette 100 can have pairs of trays 130, a pair of retaining walls 140, and an end effector 152 that enters a slot 110 through a middle gap 135 between the trays 130. Alternatively, a single tray 130 and a single retaining wall or backstop 140 per slot 110 can be utilized. In this embodiment, instead of entering a gap between a pair of trays, the end effector 152 can be configured to grasp a slide. This specification, however, refers to a cassette having a pair of trays and a pair of retaining walls for each slide for purposes of illustration and explanation.

Figure 2:
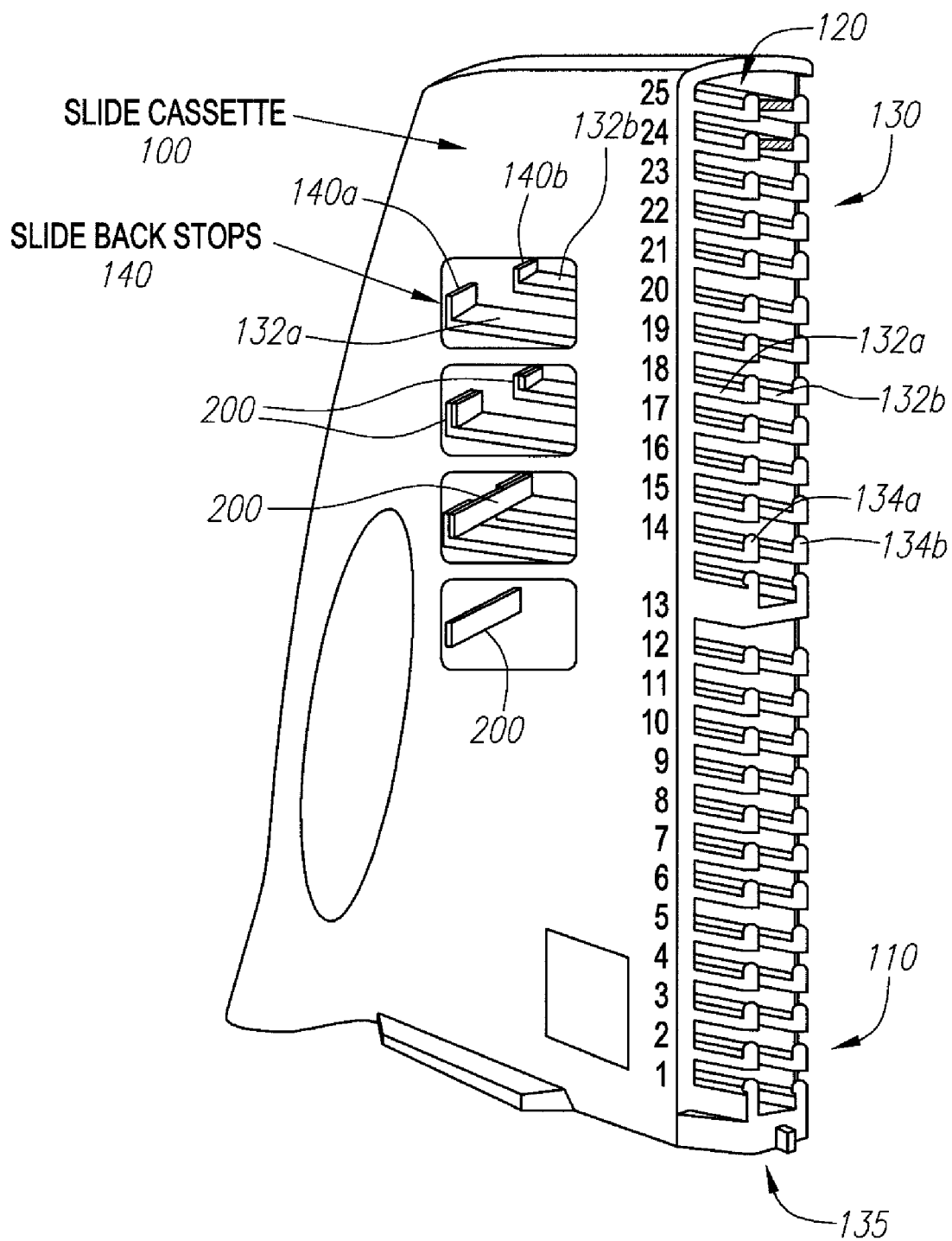
FIG. 2 is a perspective view of a cassette having a support member according to the present invention.

Turning now to FIG. 2, according to the present invention, a support member 200 (shown generally as generic support member 200) is installed inside the cassette 100. Various support members are suitable for use in the present invention, and the term "support member" as used herein generally refers to these different support members. The support member 200 retains or secures a slide 120 within the slot 110 and against the retaining lips 134, while also permitting the slide 120 to be removed from the cassette by a slide analysis machine, and re-inserted into the cassette 100 as necessary. The support member 200 can be utilized with or without the interior retaining walls 140. For example, FIG. 2 illustrates various placements of a support member within a cassette. In one embodiment, the support member extends across the retaining walls 140. This configuration may be suitable if, for example, an end effector grasps a slide instead of being inserted between a pair of trays. Alternatively, the support member 200 includes separate support member elements that are placed against the individual retaining walls 140. In yet a further alternative embodiment, the support member 120 is not attached to the retaining walls 140.

Exemplary support members 200 include, but are not limited to, one or more elastomeric bands, such as one or more rubber bands, substantially flexible foam members, springs, an insert with extensions or slide retention surfaces that function as springs, and a spring loaded support lever. Persons of ordinary skill in the art, however, will appreciate that other support members can be utilized, but for purposes of explanation and illustration, these exemplary support members are described in further detail.

Figure 3:
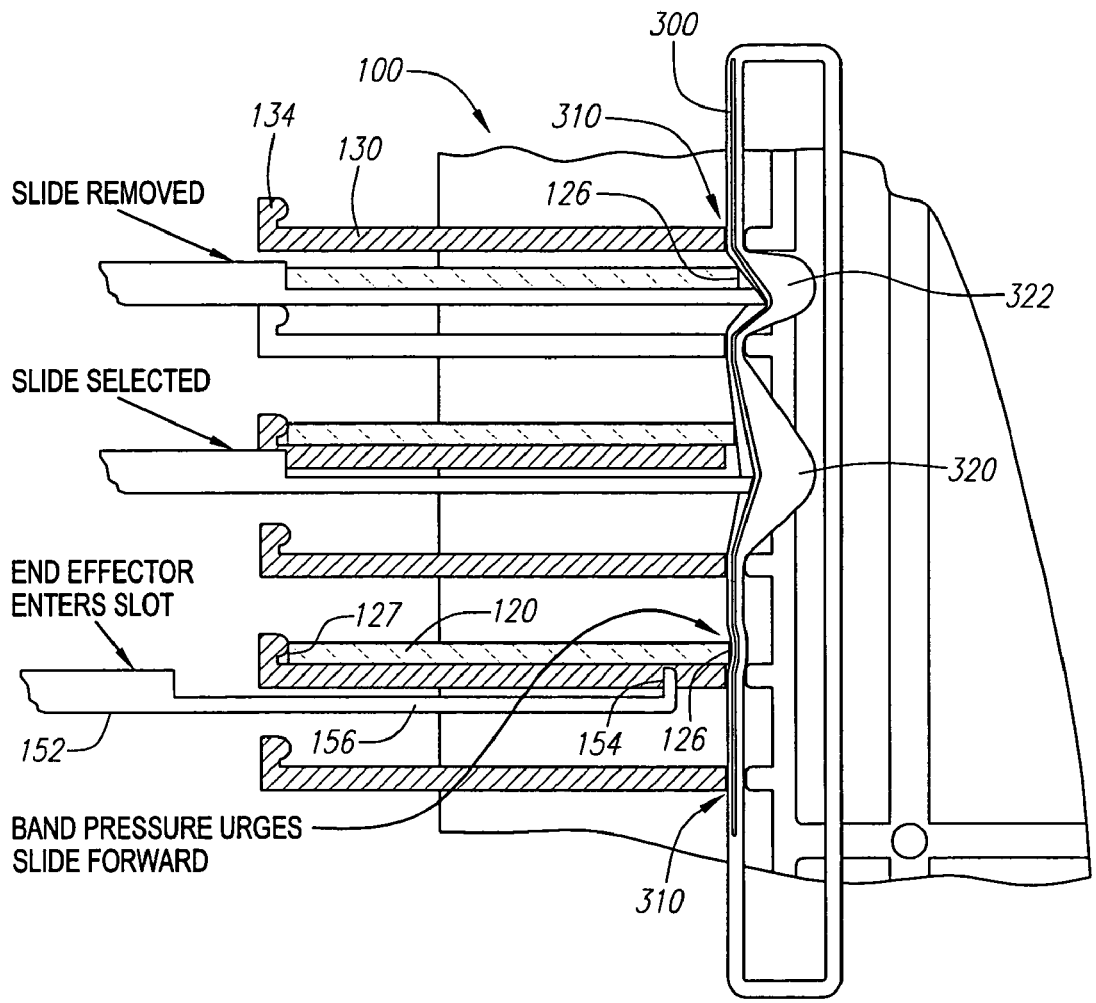
FIG. 3 is a partial cross-sectional view of a cassette having a single elastomeric support member installed through slots formed in trays of the cassette.

Referring to FIG. 3, in one embodiment of the present invention, the support member is a single, elastomeric support member 300, such as a rubber band. The rubber band 300 can be installed within the cassette 100 utilizing various mounting mechanisms. For example, as shown in FIG. 3, the rubber band 300 is inserted or weaved through apertures 310 formed within end sections of the trays 130 inside the cassette 100. A rubber band 300 can be placed through apertures of all of the trays 130 or a plurality of trays 130 (six trays are shown in FIG. 3). Preferably, the apertures 310 are vertically aligned so that the rubber band 300 is placed through the apertures 310 in a consistent manner.

The rubber band 300 is essentially divided into individual rubber band sections, one section between each of the apertures in the trays. Each section is within the horizontal or lateral path of the slide 120. In use, first edge 126 of the slide 120 contacts a section of the rubber band 300 when the slide 120 is placed in a slot 110. As a result, the band 300 is deflected. In response, the rubber band 300 exerts an opposite force upon the first edge 126 of the slide 120. The slide 120, in turn, is pushed or urged towards the retaining lips 134 so that an opposite edge 127 of the slide 120 contacts the retaining lips 134. The force exerted by the rubber band 300 is sufficient to secure or retain the slide 120 between the rubber band 300 and the retaining lips 134, while permitting the slide 120 to be removed from the cassette 100 by a slide analysis machine or end effector 152.

For example, as shown in FIG. 3, an end effector 152 enters a cassette slot 110 through a gap 135 between a pair of trays 130. The end effector 152 selects a slide and the raised edge 154 deflects the rubber band 300 (shown by deflection pattern 320) so that the raised edge 154 passes beyond the first edge 126 of the selected slide 120. The end effector 152 is then raised above the retaining lips 134 of the support trays 130. As a result, the slide 120 is placed on the top surface 156 of the end effector 152. The end effector 152 and the selected slide 120 thereon are removed from the slot 110, which may also result in deflection of the rubber band 300, as shown by deflection pattern 322. The end effector 152 can then position the slide 120 within an analysis device to examine the test sample 122.

When re-inserting slide 120 into the cassette 100 the end effector 152 and the slide 120 thereon are inserted into the slot 110 so that the raised edge deflects the rubber band 300. The end effector 152 is lowered so that the slide 120 is removed from the end effector surface 156, and the slide 120 is placed on the top surfaces 132 of the trays 130. The end effector 152 is removed from the slot 100, and the rubber band 300 contacts the first edge 126 of the slide 120. As a result, the slide 120 is removably retained between the rubber band 300 and the retaining lips 134 of the trays 130.

In an alternative embodiment of the present invention, the rubber band 300 is placed around, threaded or weaved through a plurality of mounting members within the slide cassette 100. As a result, a single rubber band 300 is divided into a plurality of support member sections, one section for each slot or slide. Each elastomeric support member section is placed in sufficient tension between the mounting members to push or urge the slide against the retaining lip 134 of the tray 130 when the support member sections are deflected.

Figure 4A:
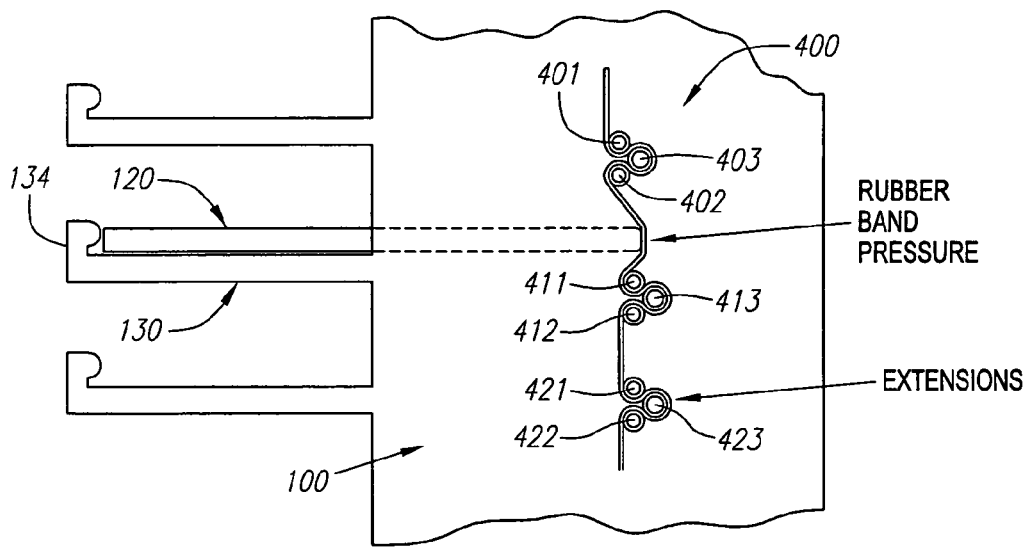
FIGS. 4A-B are partial cross-sectional views of a cassette having a single elastomeric support member secured by mounting members having mounting points arranged in a triangular configuration, and an end effector accessing a slide so secured.
Figure 4B:
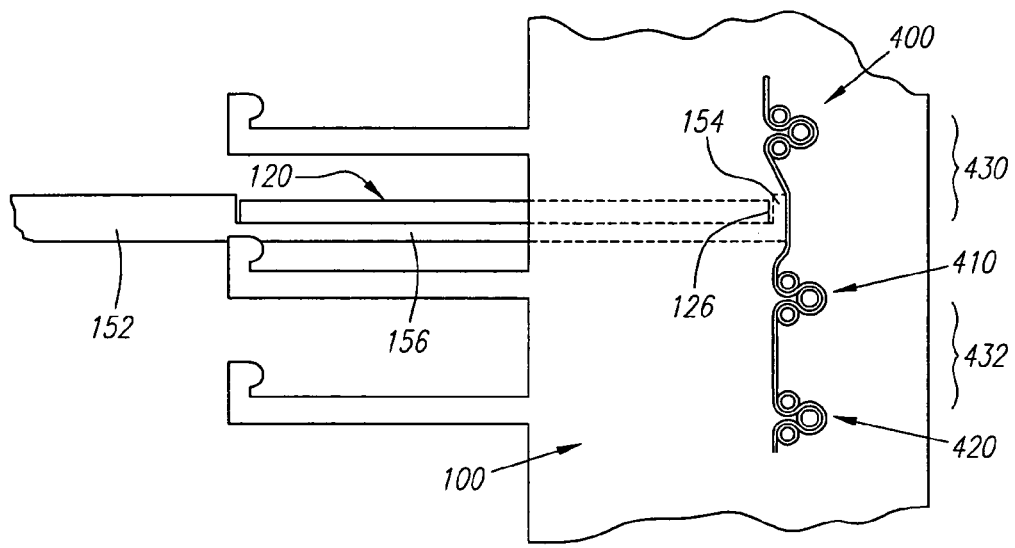

For example, referring to FIGS. 4A-B, in one embodiment, each mounting member includes three mounting points. A first mounting member 400 includes mounting points 401-403, a second mounting member 410 includes mounting points 411-413, and a third mounting member 420 includes mounting points 421-423. The three mounting points of each mounting member are arranged in a triangular configuration. The mounting points can be molded into the cassette or formed of plastic, metal, or other materials. The mounting points can also be various shapes, for example, circular mounting points as illustrated in FIGS. 4A-B.

Beginning with mounting member 410, as an example, the elastomeric support member 300 is placed partially around the first mounting point 411, between the first and the second mounting points 411 and 412, around most of the third mounting point 413 at a top of the triangular configuration, and back between a section of the elastomeric support member 300 and the second mounting point 412. As a result, the single rubber band 300 is divided into support member sections, e.g., sections 430 and 432 (generally 430) between mounting points at the base of the triangle.

As shown in FIG. 4B, an end effector 152 enters a cassette slot 110 through a gap 135 between the trays 130. The end effector 152 is inserted so that the raised end 154 deflects band section 430 and proceeds past the first edge 126 of the slide 120. The end effector 152 is then raised or elevated so that the slide 120 is placed on a top surface 156 of the end effector 152. The slide 120 can then be removed from the slot 110 by the end effector.

Figure 5A:
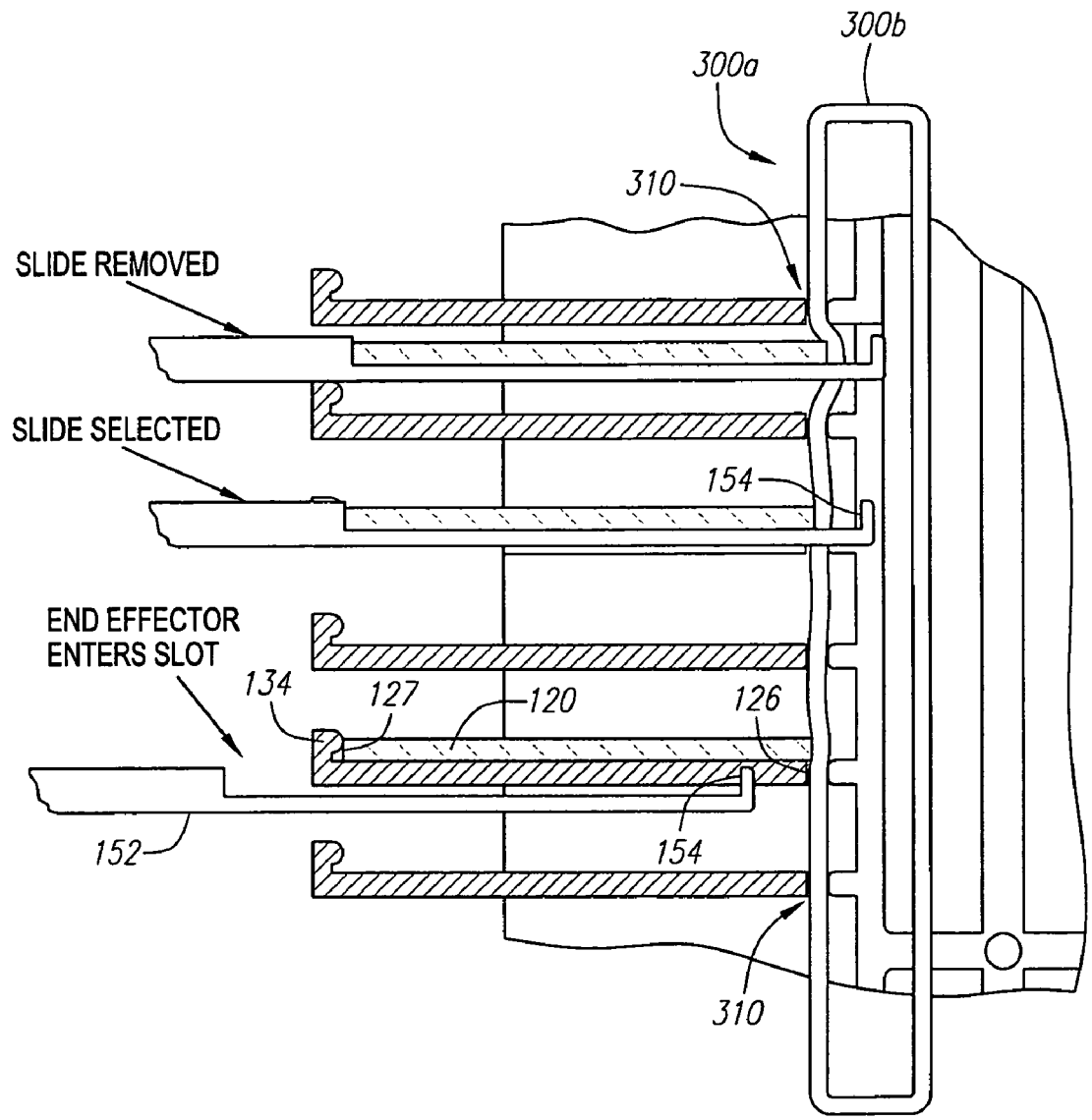
FIGS. 5A-B are top and partial cross-sectional views of a cassette having two elastomeric support members installed through slots formed in trays of the cassette.
Figure 5B:
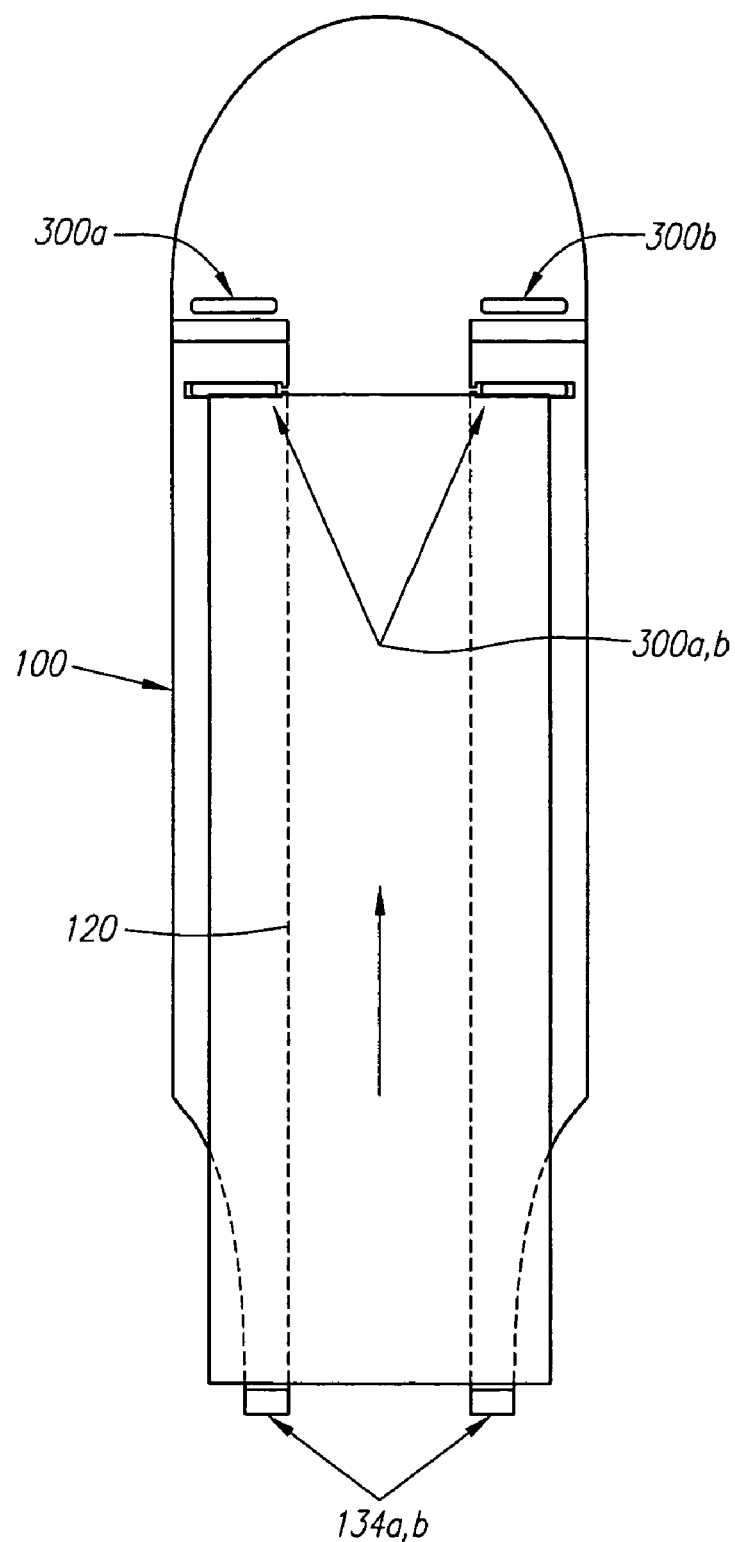

In a further alternative embodiment of the present invention, multiple elastomeric members and mounting members removably retain or secure a slide 120 within the cassette 100. For example, as shown in FIGS. 5A-B, multiple rubber bands 300a and 300b are installed within the cassette 100. A first rubber band 300a is installed through apertures in trays 130 on the left side of the slot 110, and a second rubber band 300b is installed through apertures in trays 130 on the right side of the slot 110. An end effector 152 can be inserted into the center gap 135, which is open due to the bands 300a and 300b being placed towards the left and right edges of the slot 110. The raised end 154 of the end effector 152 is inserted between the rubber bands 300a and 300b, and past the first edge 126 of the slide 120, and the slide 120 is pushed into the cassette 100 to deflect the rubber bands 300a and 300b. As a result, the opposite edge 127 of the slide is released from the retaining lips 134. The end effector 152 is then raised with the slide 120 placed on the end effector surface 156 and removed from the slot 110.

Figure 6A:
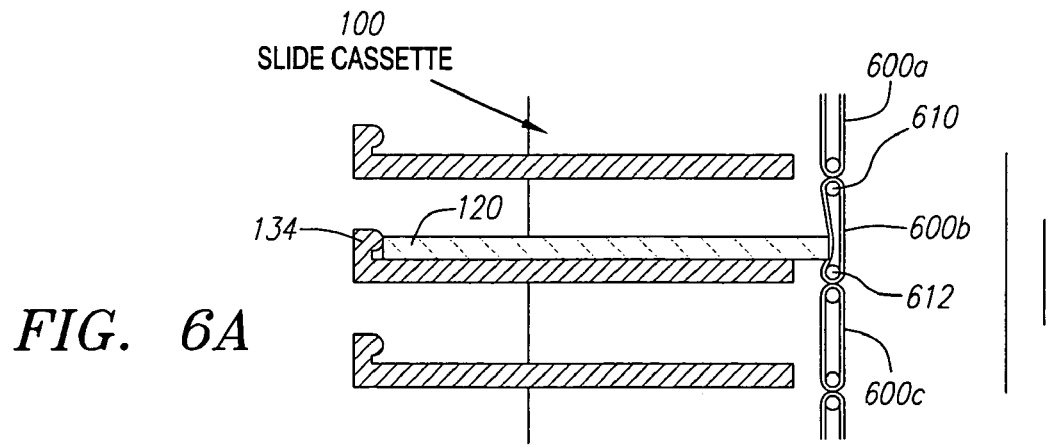
FIGS. 6A-C are partial cross-sectional views of a cassette having a plurality of elastomeric mounting members secured inside the cassette with independent and shared mounting arrangements.
Figure 6B:
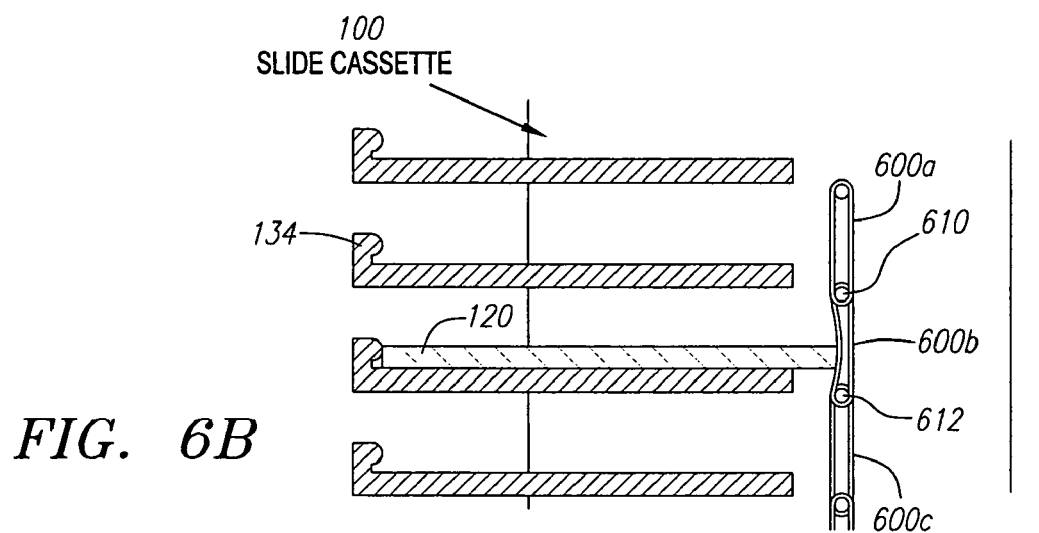
Figure 6C:
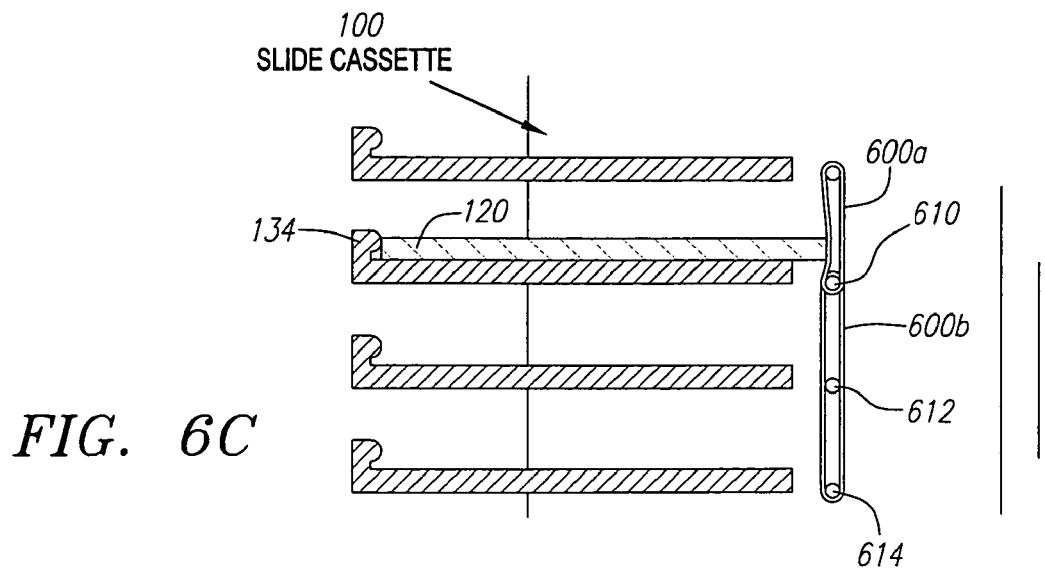

In addition to threading one or more rubber bands through slots formed in trays, in an alternative embodiment, as shown in FIGS. 6A-C, a plurality of smaller, individual rubber bands are placed around mounting members. For example, referring to FIG. 6A, a rubber band 600b is placed around dedicated mounting members 610 and 612. Rubber band 600b does not share mounting members 610 and 612 with bands 600a or 600c. The mounting members 610 and 612 are separated by a sufficient distance so that the rubber band 300b is stretched and placed in sufficient tension to urge or force a slide to contact the retaining lips 134 of the trays 130 and removably secure or retain the slide between the rubber band and the retaining lips 134.

Referring to FIG. 6B, in an alternative embodiment, one or more rubber bands 600 are placed around a mounting point that is also utilized by a different rubber band. In other words, two or more rubber bands share the same mounting point. For example, bands 600a and 600b share mounting point 610, and bands 600b and 600c share mounting point 612.

As shown in FIG. 6C, in a further alternative embodiment, one or more rubber bands extend across one or more mounting points and share a mounting point with another rubber band. For example, rubber bands 600a and 600b share mounting point 610, and rubber band 600b is placed around mounting points 610 and 614, passing over mounting point 612. This extended rubber band configuration may be appropriate if the extended rubber band is placed in sufficiently high tension between the end mounting points to provide a sufficient force to their respective slides when they contact the extended rubber band.

Figure 7:
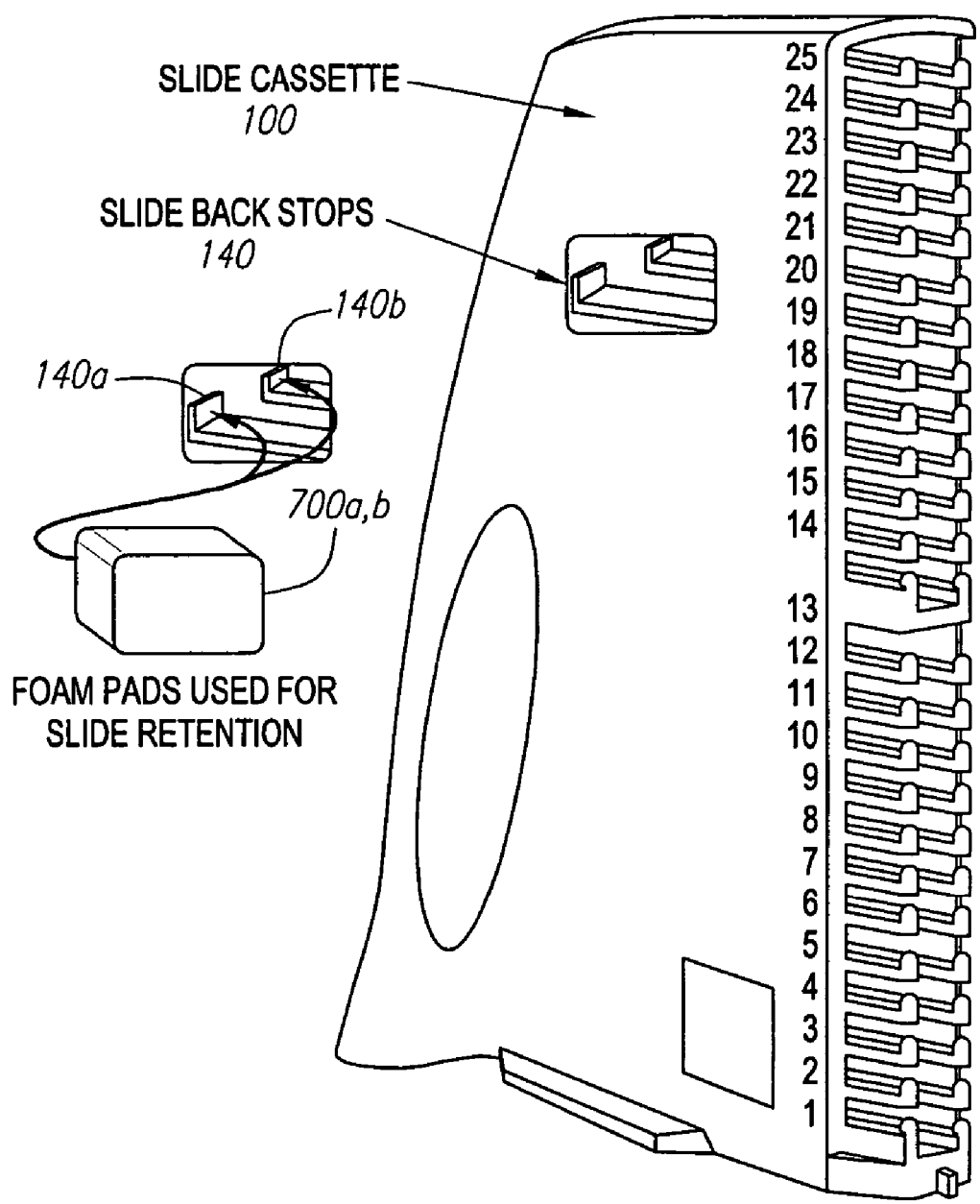
FIG. 7 is a perspective view of a cassette having foam support members attached to slide retaining members within the cassette.

In yet a further alternative embodiment, as shown in FIG. 7, the support member includes substantially flexible foam support members 700a and 700b (generally 700). The foam members 700 are installed against the retaining walls 140 that limit how far the slide 120 can move within the cassette 100. The slide contacts the foam members 700 and, as a result, the foam members 700 provide a force in the opposite direction and urge an opposite edge 127 of the slide 120 against the retaining lips 134 of the trays 130. Thus, the slide 120 is removably secured between the foam members 700 and the retaining lips 134. The stiffness or flexibility of the foam members 700 can vary to provide different retaining forces. Rubber inserts can also be installed against the retaining walls instead of foam members.

Figure 8C:
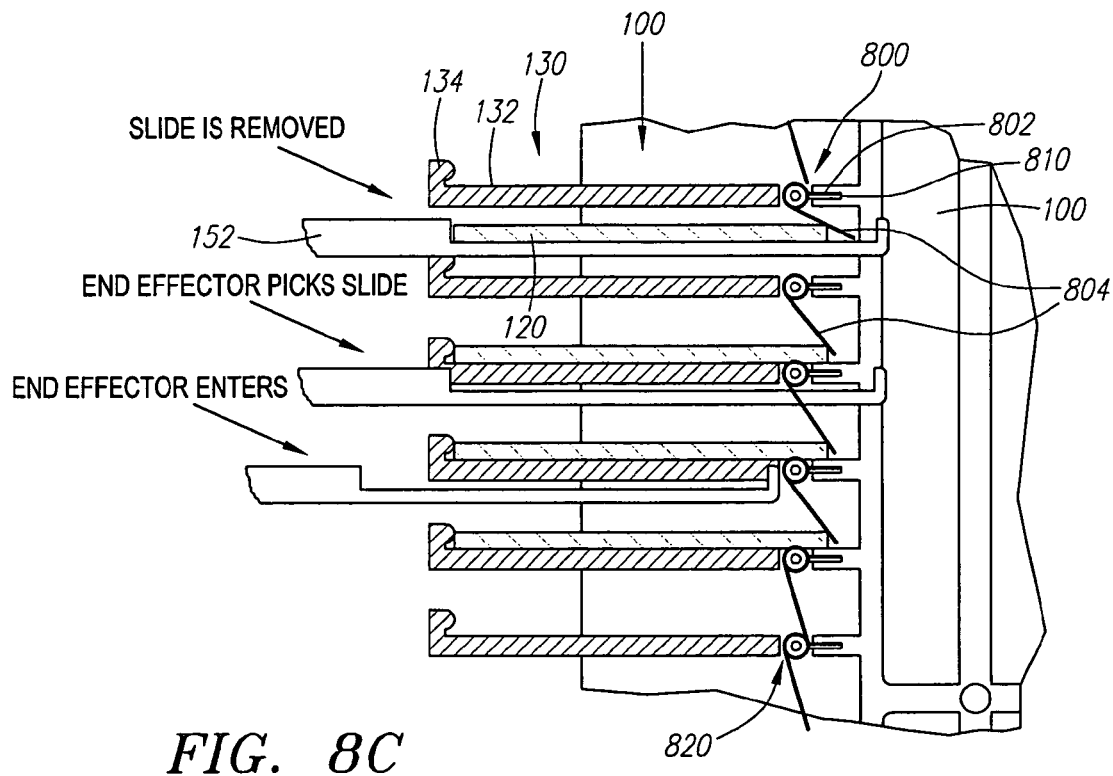

In yet a further alternative embodiment of the present invention, as shown in FIGS. 8A-C, the support members within the cassette are springs 800a and 800b (generally spring 800), such as coiled metal or plastic springs. FIG. 8A illustrates a top view of springs 800 installed within a tray 130 in aperture 820. Specifically, the view shown in FIG. 8A is a view from above the subject slide, including the support trays 130, which holds the next slide above. Thus, the slide 120 being supported or retained by the springs 800 is shown below the trays 130.

Referring to FIG. 8B, a flanges 802 of the springs 800 are inserted and mounted within apertures 810a-b (generally aperture 810) formed in the rear section of a tray 130. The end or deflectable members 804a and 804b (generally deflectable member 804) of the springs 800 are placed within the path of a slide 120. The slide 120 is removably retained within the cassette 100 between the deflectable spring members 804 of the springs 800 and the retaining lips 134 of the trays 130.

As shown in FIGS. 8B-C, the end effector 152 enters a cassette slot 110 through a gap 135 between a pair of trays 130 and springs 800. As a result, the end members 804 are deflected, and the springs 800 are compressed or coiled. In response, the springs 800 provide a re-coiling force in the opposite direction, urging the opposite end 127 of the slide 120 to contact the retaining lips 134 of the trays 130. Thus, the slide 120 is removably secured or retained between the retaining lips 134 and the ends 804 of the springs 800.

Figure 9A:
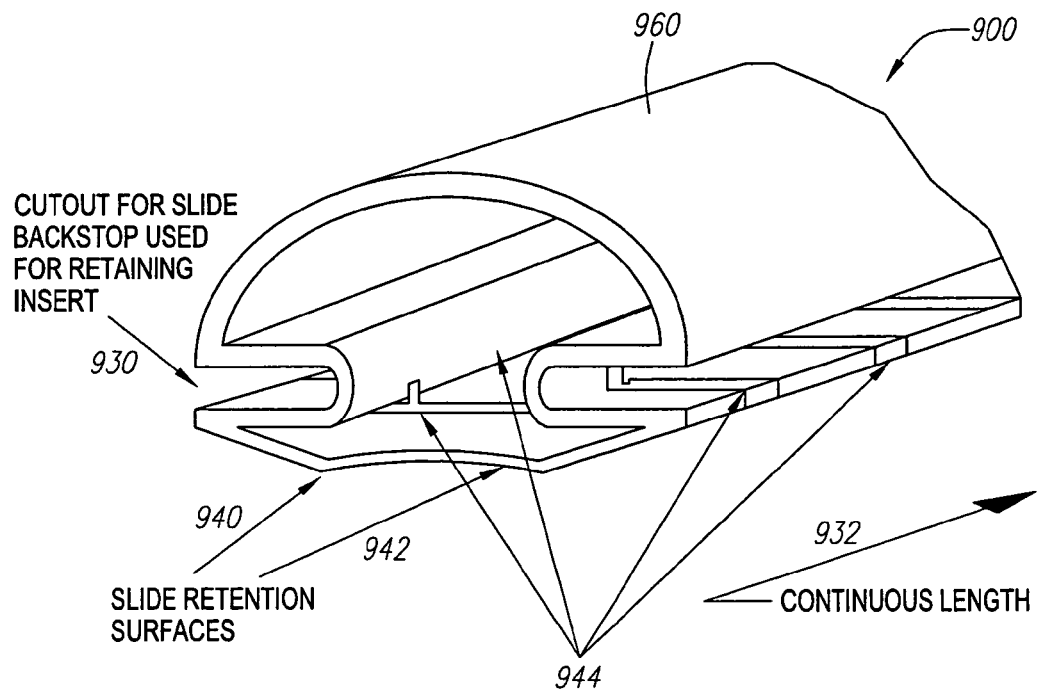
FIG. 9A-B are perspective and top views of an insert for retaining a slide.
Figure 9B:
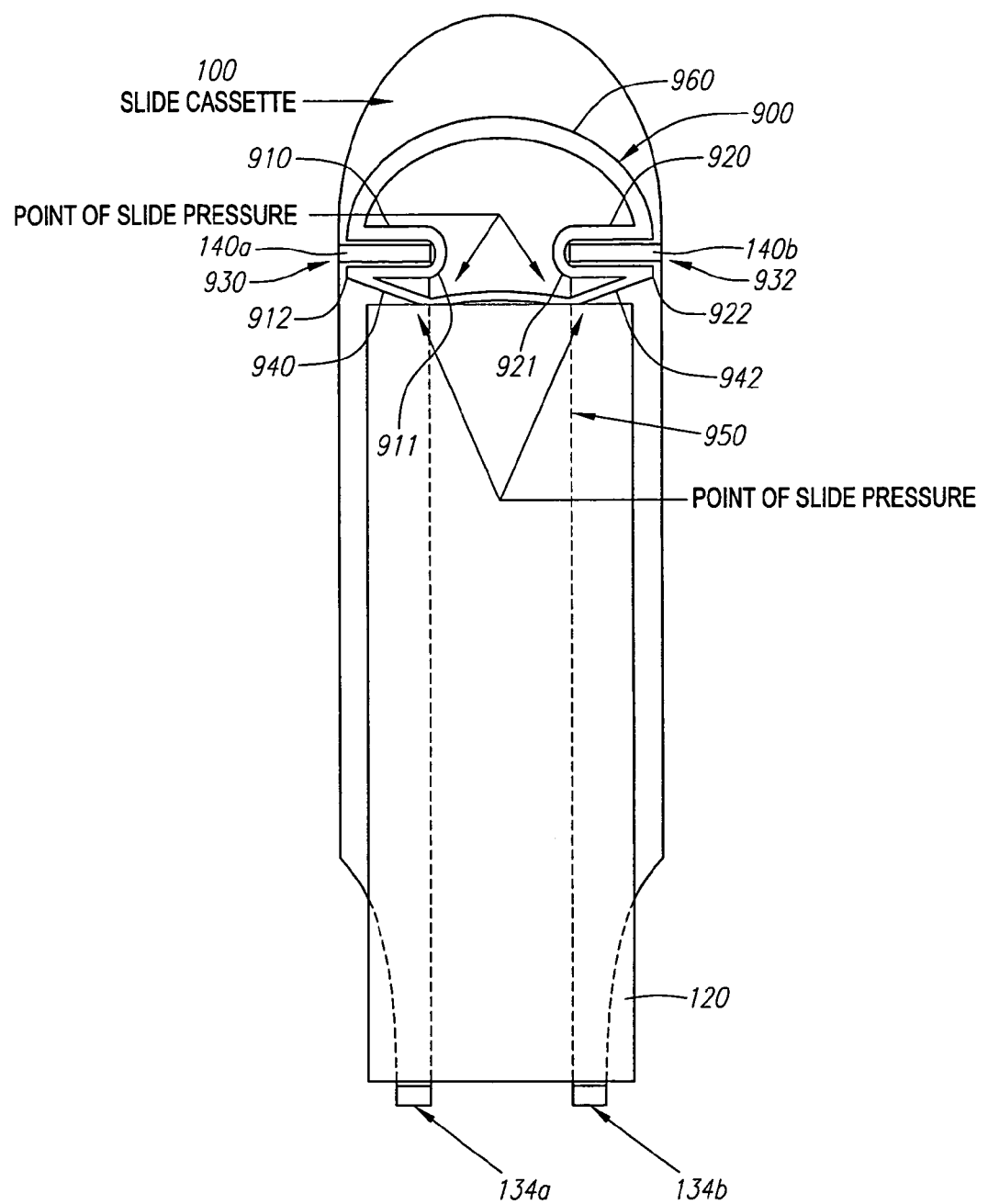

FIGS. 9A-B show yet a further alternative embodiment of the support member according to the present invention. This support member is an insert 900, such as a molded, plastic or polymer insert, that is installed within the cassette 100. The insert 900 can extend for the entire length of the cassette 100, or a portion thereof, providing support to different numbers of slides.

The insert 900 includes surfaces 910-912 and 920-922 that define grooves 930 and 932. The retaining walls 140a and 140b are inserted into the grooves 930 and 932. Thus, the retaining walls 140 limit the movement of the slide 120 into a cassette slot 110, while also serving to mount the insert 900 in the cassette 100.

The insert 900 includes extensions or retention surfaces 940 and 942 (generally 940) that function as springs. The extensions 940 and 942 extend from the edges of the groove-defining surfaces 912 and 922. The extensions 940 contact the first edge 126 of slide 120 when the slide 120 is placed in the slot 110. When the extensions 940 and 942 are compressed towards surfaces 912 and 922, they provide a force in the opposite direction to urge an opposite edge of the slide 120 to contact the retaining members 134. Additionally, the slots or ridges 944 within the insert 900 can be used to provide variable pressure to a slide retained within the insert 900. Thus, the slide 120 is removably retained or secured between the retaining lips 134 and the extensions 940 of the insert 900.

The insert 900 can optionally include a middle section 950 between the extensions 940. The middle section 950 also contacts the first edge 126 of the slide 120 when the slide 120 is placed in the slot 110. The top portion 960 of the exemplary insert 900 is shown as having an arcuate shape that joins surfaces 910 and 920. Other top portion 960 shapes can be used for purposes of installing the insert 900 within the cassette 110.

Figure 10A:
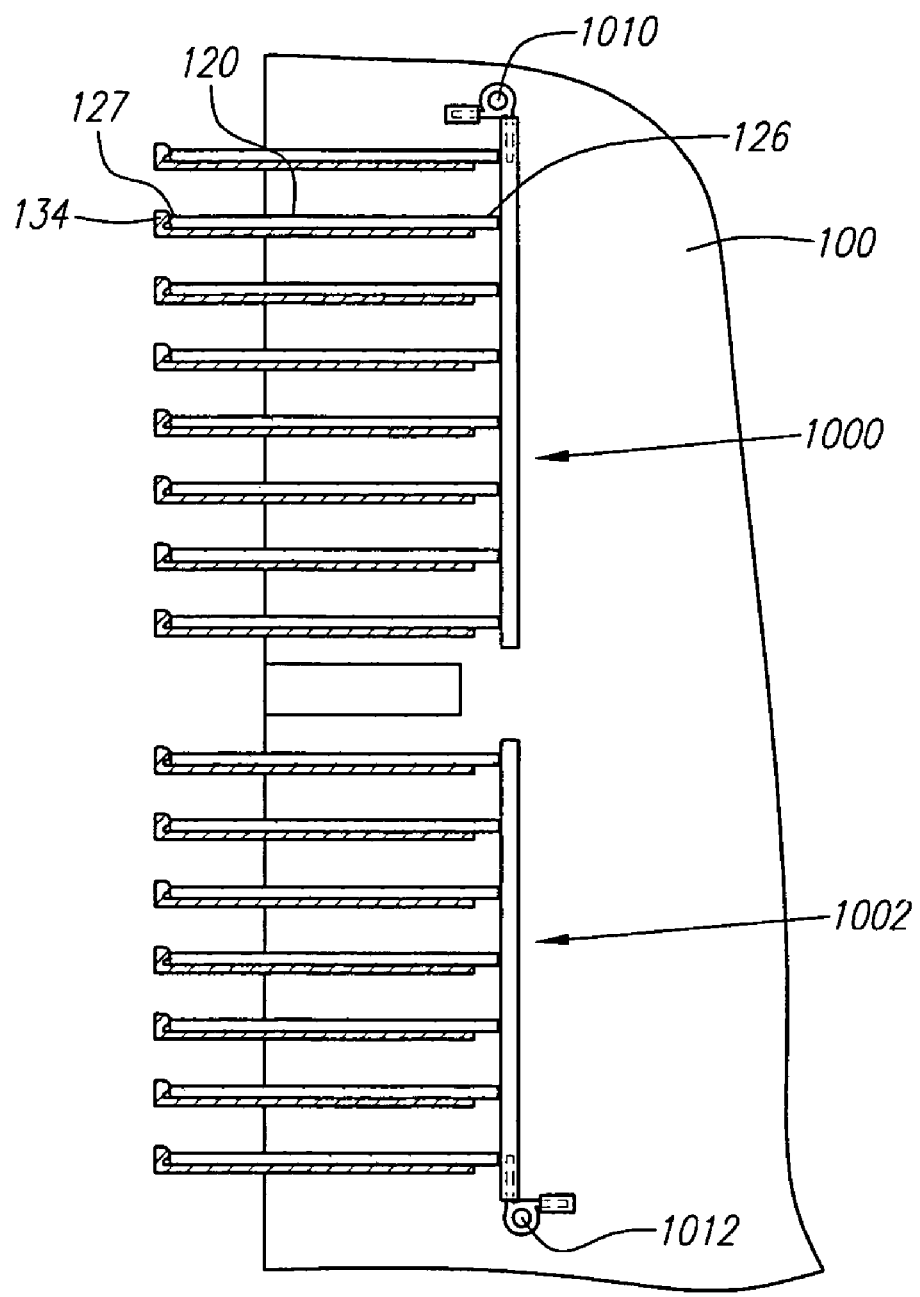
FIGS. 10A-B are cross-sectional views of spring-loaded levers for retaining a slide.

FIG. 10A illustrates a further alternative embodiment of the present invention. Levers 1000 and 1002 (generally 1000) are inserted within the cassette 110. Each lever 1000 extends for a length of the cassette 100, for example, half of the cassette 100. The lever 1000 spans slots 1-13, and the lever 1002 spans slots 14-25. The levers 1000 and 1010 are attached to respective springs 1010 and 1012 (generally 1010) within the cassette 100. Spring 1010 is located at the top of the cassette 100, and spring 1012 is located at the bottom of the cassette 100.

A lever 1000 and a spring 1010 are configured so the spring 1010 exerts a force on the lever 1000 so the lever 1000 contacts a first edge 126 of the slide 120. As a result, all of the slides 120 within slots 1-13 are retained between the lever 1000 and the retaining members 134, and all of the slides 120 within slots 14-25 are retained between the lever 1002 and the retaining members 134. Different numbers of levers 1000 and 1002 can also be utilized with different cassette 100 configurations to support different numbers of slides 120.

Figure 10B:
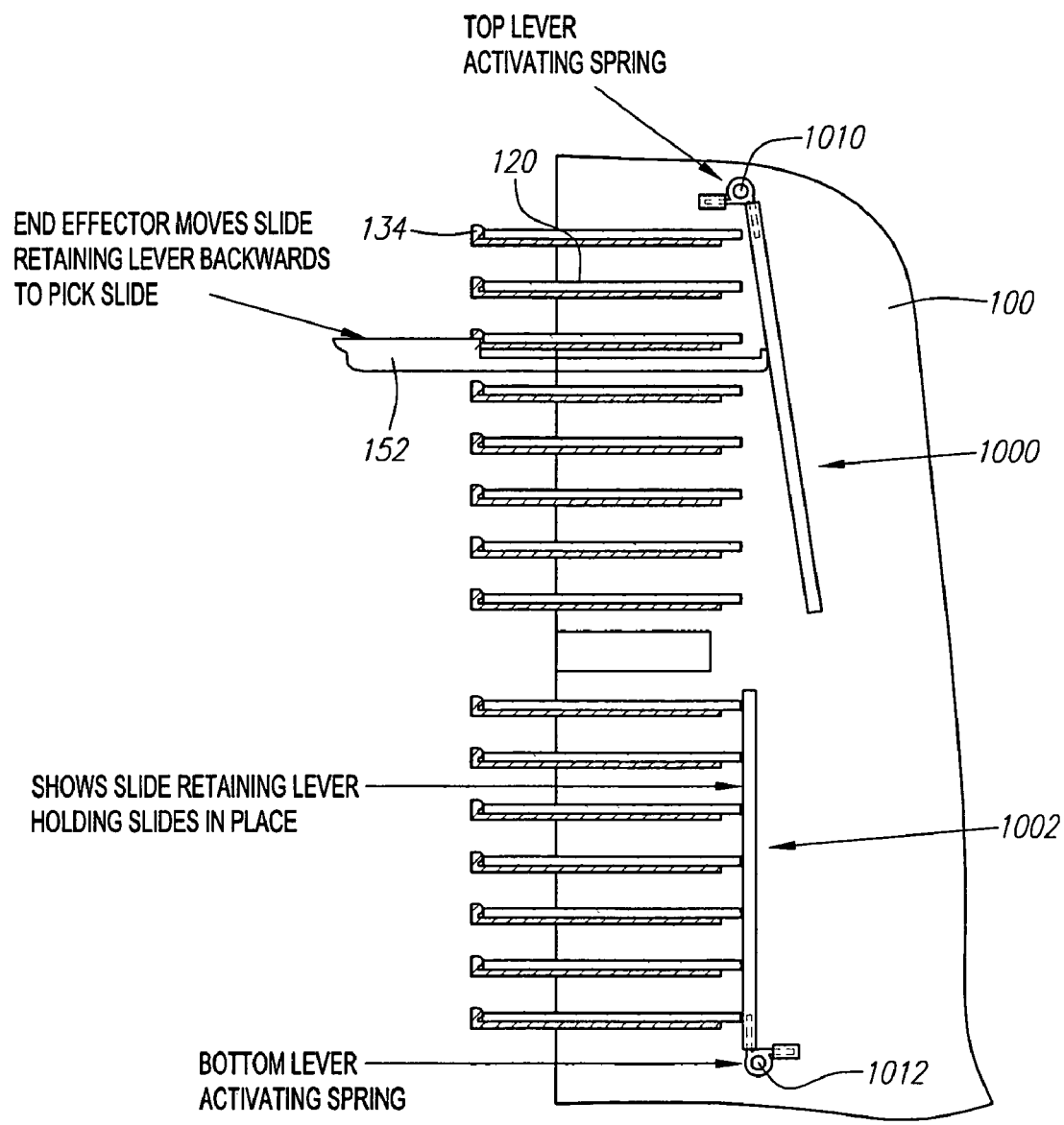

In use, as shown in FIG. 10B, an end effector 152 is inserted into the cassette and engages or pushes against a lever 1000, thereby coiling or compressing a spring 1010. As a result, the lever 1000 is displaced away from the slides, so that slides 120 that were previously supported by the lever 1000 are released and can be removed from their slots 110.

Figure 11:
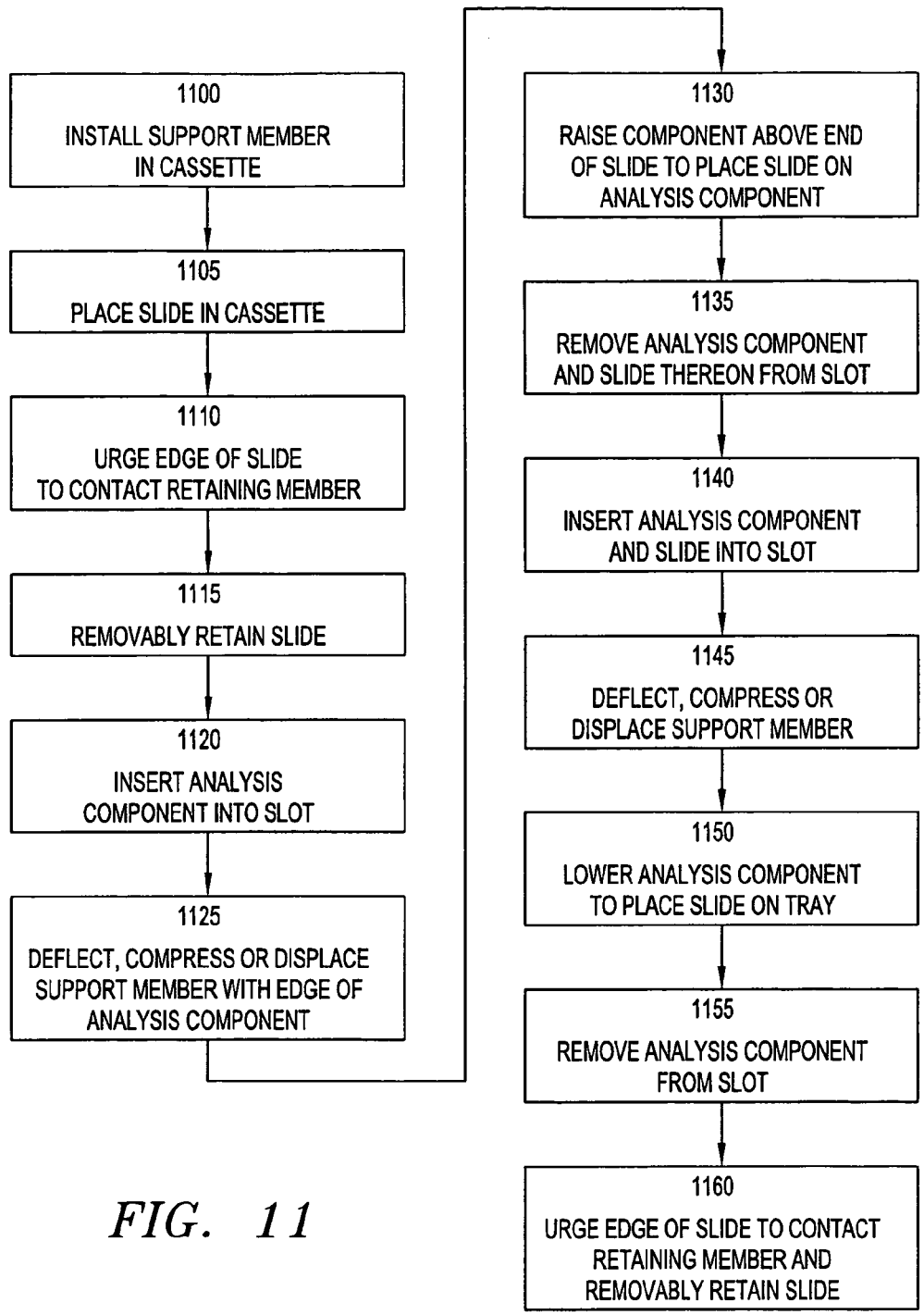
FIG. 11 is a flow diagram illustrating a process for removably retaining and removing a slide from a cassette.

Referring to FIG. 11, having described various support member configurations, following is a flow diagram illustrating the manner in which a slide can be removably retained or secured between a support member and a retaining member of a cassette tray and the manner in which an analysis system removes a slide so secured from the cassette.

Initially, in step 1100, a support member is installed within the cassette. In step 1105, a slide is placed in a cassette slot so that a first edge of the slide contacts the support member. In step 1110, the support member provides a force to the slide in an opposite direction and urges an opposite edge of the slide to contact the retaining lips of the trays. In step 1115, the slide is removably retained on the trays between the support member and the retaining lips of the trays.

Continuing with step 1120, an analysis system component, such as an end effector, is inserted into a slot. For example, in the exemplary system described in this specification, the end effector is inserted into a slot between a pair of trays that hold a slide. In step 1125, a raised edge of the end effector engages and deflects, compresses or displaces the support member beyond the first edge of the slide. In step 1130, the end effector is raised or elevated so that the raised edge of the end effector rises above the first end of the slide, and the slide is placed on top of the end effector. In step 1135, the end effector and the slide thereon are removed from the slot above the retaining lips of the trays.

In step 1140, following any testing or analysis of the sample on the slide, the end effector and the slide thereon can be re-inserted into the slot. In step 1145, the raised edge of the end effector deflects, compresses or displaces the support member so that the slide contacts the slide stops within the cassette. In step 1150, the end effector is lowered so that the slide is placed on the trays. In step 1155, the end effector is removed from the slot. In step 1160, the support member contacts the first edge of the slide and urges an opposite edge of the slide to contact the retaining lips of the tray. As a result, the slide is removably retained on the tray between the retaining lips and the support member.

The previously described configurations and method are advantageous over conventional systems and slide storage and processing methods. For example, cassette slots are typically larger than the slides they hold. As a result, however, slides in conventional systems may float freely within the cassette slot and upon their support trays. The present invention overcomes these shortcomings by retaining or securing the slide on the tray while, at the same time, permitting the slide to be removed from the tray and re-inserted as needed. Further, the extent to which cassettes with slides can be maneuvered is improved with the present invention since the slides are less likely to shift within the cassette for fall from the tray.

The present invention is also advantageous since it provides for more accurate and efficient slide sensing. For example, conventional systems typically permit the slides to shift or rotate clockwise or counter-clockwise within the slot, move to the front or back of a slot, or rest on top of the retaining lips. The ability of a slide processing system to accurately retrieve slides that have moved from the original or intended positions is typically impaired. Further, such errors can result in damage to the slides if the system attempts to retrieve a misaligned slide, for example, when an end effector drives through an overhanging slide and breaks the slide. The present invention, however, reduces or eliminates these problems since the slides are retained within the cassette. The present invention also reduces or eliminates the need for more sensitive (and often more expensive) equipment that is required to process slides that are aligned, misaligned, or otherwise shifted out of their proper positions.

Having described the apparatus for removably retaining or securing a slide within a cassette according to the present invention, persons of ordinary skill in the art will recognize that the above apparatus can be modified in various ways to perform the same retaining functions. For example, other support members can be installed within a cassette to achieve the recited functions. Moreover, different numbers of support members can be utilized, as well as different numbers of mounting members or mounting points as needed. Additionally, although a triangular configuration of mounting points was described in connection with a single elastomeric band, other configurations can be utilized to achieve the same result. Accordingly, persons of ordinary skill in the art will appreciate that the invention is not limited to the particular exemplary embodiments described, but rather, the invention encompasses various other support member and cassette configurations.

Although references have been made in the foregoing description to various embodiments, persons of ordinary skill in the art will recognize that insubstantial modifications, alterations, and substitutions can be made to the described embodiments without departing from the invention as recited in the accompanying claims.

What is claimed is:

1. A slide cassette, comprising:
   a storage receptacle defining a slot configured for receiving a microscope slide;
   a tray extending within the storage receptacle below the slot, the tray being configured to support the microscope slide and having a retaining member at an end thereof;
   at least one stop that limits movement of the microscope slides in the slot; and
   an insert defining grooves for receiving the at least one slide stops therein to secure the insert within the storage receptacle, the insert including a pair of extensions that function as springs, such that, when the microscope slide is received within the slot, a first edge of the microscope slide contacts the extensions, and the extensions urge an opposite edge of the microscope slide to contact the retaining members, thereby removably retaining the microscope slide on the tray between the retaining members and the extensions.

2. The slide cassette of claim 1, wherein the extensions extend from surfaces that define the grooves.

3. The slide cassette of claim 1, wherein the insert has a middle section between the extensions, the first edge of the microscope slide contacting the extensions and the middle section when the microscope slide is received in the slot.

4. The apparatus of claim 1, wherein the insert has a closing section joining surfaces defining the grooves, the closing section being located on an opposite side of the grooves relative to the extensions.

5. A slide cassette, comprising:
   a storage receptacle defining a slot configured for receiving a microscope slide;
   a tray extending within the storage receptacle below the slot, the tray being configured to support the microscope slide and having at least one retaining member at an end thereof;
   a spring located within the storage receptacle; and
   a lever attached to the spring, such that, when the microscope slide is received within the slot, a first edge of the microscope slide contacts the lever, and the spring applies a force to the lever to urge an opposite edge of the microscope slide to contact the at least one retaining members, thereby removably retaining the microscope slide on the tray between the at least one retaining member and the lever.

6. The slide cassette of claim 5, wherein the microscope slide is configured for being released by displacing the lever and compressing the spring.

7. The slide cassette of claim 5, wherein the storage receptacle defines a plurality of slots configured for respectively receiving a plurality of microscope slides, wherein the lever is configured for contacting first edges of the microscope slides.

8. A slide cassette, comprising:
   a storage receptacle defining a slot configured for receiving a microscope slide;

a tray extending within the storage receptacle below the slot, the tray being configured to support the microscope slide and having at least one retaining member at an end thereof;

an elastomeric support member in communication with the slot; and a plurality of mounting members, the elastomeric support member being weaved through the plurality of mounting members to define a plurality of support member sections, such that, when the microscope slide is received in the slot, a first edge of the microscope slide contacts one of the support member sections, and the one support member section urges an opposite edge of the microscope slide to contact the at least one retaining member, thereby removably retaining the microscope slide on the tray between the at least one retaining member and the one support member section.

9. The slide cassette of claim 8, wherein some or all of the elastomeric support member sections are placed in tension.

10. A slide cassette, comprising:

a storage receptacle defining a slot configured for receiving a microscope slide;

a tray extending within the storage receptacle below the slot, the tray being configured to support the microscope slide and having at least one retaining member at an end thereof;

an elastomeric support member in communication with the slot; and a plurality of mounting members, the elastomeric support member being disposed around two or more mounting members, and wherein the two or more mounting members each includes first, second and third mounting points, the respective mounting points of each mounting member being arranged in a triangular configuration, such that, when the microscope slide is received in the slot, a first edge of the microscope slide contacts the elastomeric support member, and the elastomeric support member urges an opposite edge of the microscope slide to contact the at least one retaining member, thereby removably retaining the microscope slide on the tray between the at least one retaining member and the elastomeric support member.

11. The slide cassette of claim 10, wherein for each mounting member, the elastomeric support member is placed partially around the first mounting point, between the first and the second mounting points, around the third mounting point at a top of the triangular configuration, and between a section of the elastomeric support member and the second mounting point.

12. The slide cassette of claim 10, wherein a support member section is formed between mounting points at a base of the triangular configuration.

13. The slide cassette of claim 10, wherein a single elastomeric support member is weaved through the plurality of mounting points arranged in a triangular configuration to form a plurality of elastomeric support member sections.

* * * * *